United States Patent
Kuwata (10) Patent No.: US 7,995,193 B2
(45) Date of Patent: Aug. 9, 2011

(54) MEASURING DEVICE

(75) Inventor: Yasuaki Kuwata, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 58 days.

(21) Appl. No.: 12/512,150

(22) Filed: Jul. 30, 2009

(65) Prior Publication Data

US 2010/0177300 A1      Jul. 15, 2010

(30) Foreign Application Priority Data

Jan. 9, 2009   (JP) .................................. 2009-003976

(51) Int. Cl.
*G01P 3/36* (2006.01)
(52) U.S. Cl. .......................................... 356/27; 356/28
(58) Field of Classification Search .................. 356/27, 356/28, 614
See application file for complete search history.

(56) References Cited

U.S. PATENT DOCUMENTS

| | | | |
|---|---|---|---|
| 5,793,485 A * | 8/1998 | Gourley | 356/318 |
| 6,624,899 B1 * | 9/2003 | Clark | 356/614 |
| 6,844,537 B2 * | 1/2005 | Wilson et al. | 250/206.1 |
| 6,860,350 B2 * | 3/2005 | Beuhler et al. | 180/167 |
| 6,875,993 B2 * | 4/2005 | Tatum et al. | 250/559.2 |
| 7,202,942 B2 * | 4/2007 | Deines | 356/28.5 |
| 7,466,398 B2 * | 12/2008 | Cheng et al. | 356/28 |
| 7,567,341 B2 * | 7/2009 | Dolfi et al. | 356/28 |
| 7,671,972 B2 * | 3/2010 | Cheng et al. | 356/28 |
| 7,675,630 B2 * | 3/2010 | Teo et al. | 356/614 |
| 2002/0141472 A1 | 10/2002 | Koyama et al. | |
| 2006/0120426 A1 | 6/2006 | Kuwata | |
| 2008/0174787 A1 * | 7/2008 | Teo et al. | 356/614 |
| 2008/0198357 A1 * | 8/2008 | Cheng et al. | 356/28 |
| 2008/0297809 A1 * | 12/2008 | Holzapfel et al. | 356/614 |
| 2010/0069727 A1 * | 3/2010 | Kawano et al. | 600/310 |

FOREIGN PATENT DOCUMENTS

| | | |
|---|---|---|
| JP | 04-109938 | 4/1992 |
| JP | 11-287860 | 10/1999 |
| JP | 2002-350544 | 12/2002 |
| JP | 2002-359432 | 12/2002 |
| JP | 2004-513348 | 4/2004 |
| JP | 2004-288674 | 10/2004 |
| JP | 2006-100858 | 4/2006 |
| WO | 02/37124 | 5/2002 |

OTHER PUBLICATIONS

IEICE Trans. Electron., vol. E85-C, No. 4, Apr. 2002, pp. 995-1000.

* cited by examiner

*Primary Examiner* — Roy Punnoose
(74) *Attorney, Agent, or Firm* — Fildes & Outland, P.C.

(57) ABSTRACT

A measuring device includes a VCSEL of a first-order or high-order single mode emitting laser beams, a driving part configured to drive the VCSEL, a detecting part configured to detect an electric signal relating to feedback lights generated when laser beams are projected onto an object, and a calculating part configured to identify a direction of movement of the object on the basis of the electric signal detected by the detecting part.

8 Claims, 11 Drawing Sheets

LP21 MODE

LP21 MODE

MEASURING DEVICE

CROSS-REFERENCE TO RELATED APPLICATION

This application is based on and claims priority under 35 USC 119 from Japanese Patent Application No. 2009-003976 filed Jan. 9, 2009.

BACKGROUND

1. Technical Field

The present invention relates to a measuring device.

2. Related Art

There is a measuring device that utilizes a semiconductor laser to precisely detect the position or velocity of an object in a non-contact fashion. The measuring device has a specific type called self-coupling effect or self-mixing effect and applies the behavior of the semiconductor laser responsive to feedback lights reflected or scattered by the object to the measurement. The self-coupling effect means that the feedback lights or reflected lights are amplified in a laser medium, and are thus caused to modulate the laser oscillation.

SUMMARY

According to an aspect of the invention, there is provided a measuring device includes a Vertical-Cavity Surface-Emitting Laser (VCSEL) of a first-order or high-order single mode emitting laser beams, a driving part configured to drive the VCSEL, a detecting part configured to detect an electric signal relating to feedback lights generated when laser beams are projected onto an object, and a calculating part configured to identify a direction of movement of the object on the basis of the electric signal detected by the detecting part.

DETAILED DESCRIPTION

A description will now be given, with reference to the accompanying drawings, of exemplary embodiments of the present invention.

Figure 1:
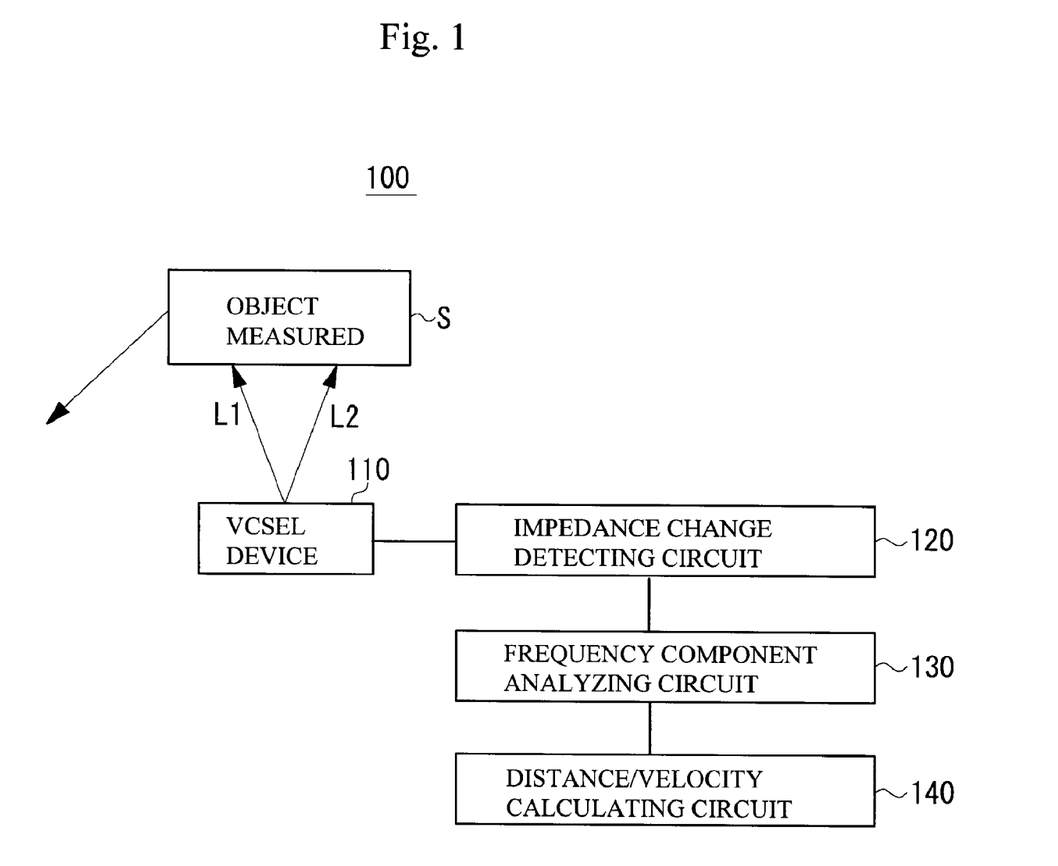
FIG. 1 is a block diagram a measuring device in accordance with an exemplary embodiment.

FIG. 1 is a block diagram of a measuring device in accordance with an exemplary embodiment. A measuring device 100 includes a VCSEL (Vertical-Cavity Surface-Emitting Laser) device 110, an impedance change detecting circuit 120, a frequency component analyzing circuit 130 and a distance/velocity calculating circuit 140. The VCSEL device 110 is capable of emitting two divided laser beams. The impedance change detecting circuit 120 detects a change of the impedance of the VCSEL device 110 in which the light intensity is modulated by the feedback lights reflected or scattered by an object S to be measured. The frequency component analyzing circuit 130 analyzes the frequency components in the impedance change detected by the impedance change detecting circuit 120. The distance/velocity calculating circuit 140 calculates the distance to the measured object S, the velocity of the measured object S and the direction in which the measured object S moves. The circuits 120 through 140 may be formed as a single integrated circuit or may be implemented on a single semiconductor chip. The measuring device 100 may be housed in a single package or module in which the VCSEL device 110 is incorporated with the circuits 120 through 140.

Figure 2:
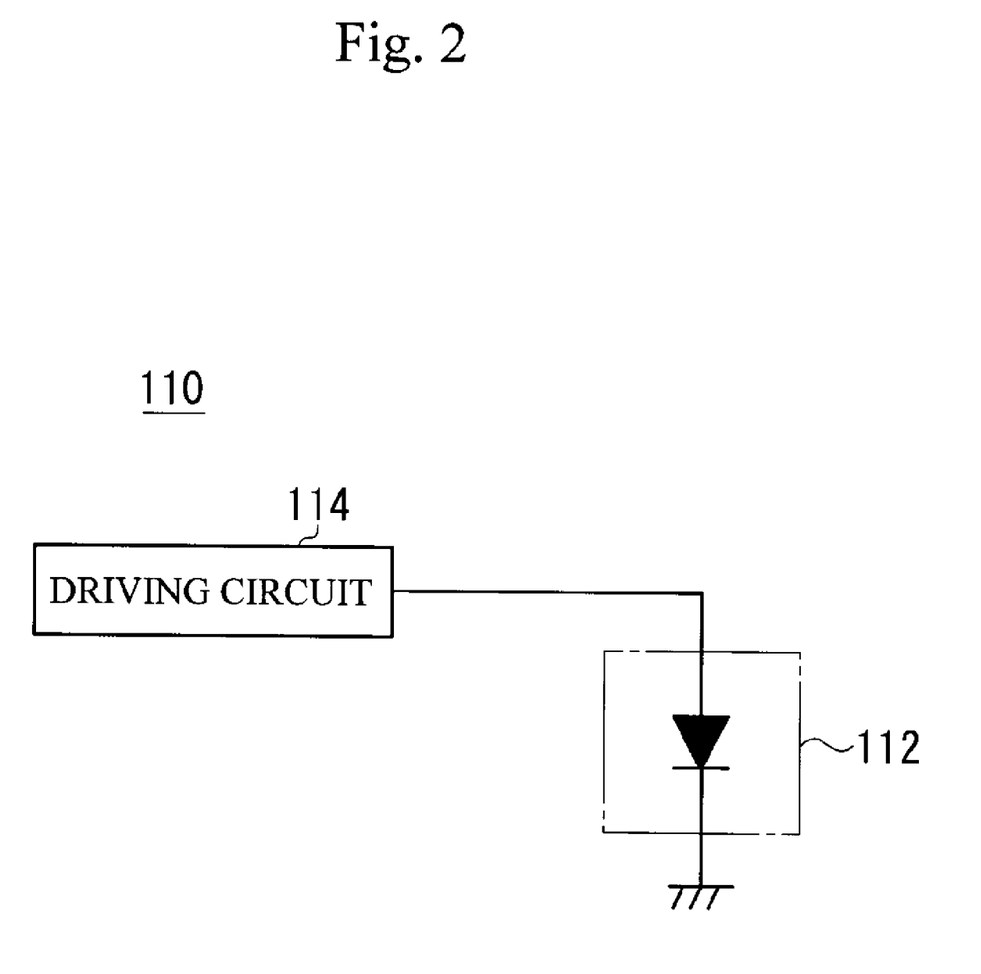
FIG. 2 is a block diagram of a VCSEL device illustrated in FIG. 1.

As illustrated in FIG. 2, the VCSEL device 110 includes a first-order single-mode VCSEL 112, and a driving circuit 114 that drives the VCSEL 112. The driving circuit 114 supplies the VCSEL 112 with a driving signal, which may be a triangular wave or saw tooth wave having a predetermined constant period. The VCSEL 112 emits two laser beams having the light intensities that are varied in response to frequency changes of the driving signal. The first-order single mode is a transverse mode oscillation and emits laser light composed of two single-peak laser beams having a little variation in the spreading angle with respect to the optical axis. The first-order single mode may be obtained by suppressing or shielding the zero-order laser light by forming a trench or groove in a contact layer of an upper reflection film having a semiconductor multilayer structure or arranging the upper reflection film so that a part of an electrode pattern formed on the contact layer remains in the center.

The first-order single-mode VCSEL may be manufactured by a method described in "IEICE TRANS. ELECTRON, VOL. E85-C, NO. 4 Apr. 2002". The first-order single-mode VCSEL may be manufactured by determining the core diameter of the resonator, and the size and shape of an emission aperture of an electrode corresponding to an emission pattern defined by the core diameter of the resonator. That is, the modes other than the first-order mode, namely, the second-order mode and higher-order modes are suppressed or shielded by filtering.

Figure 3:
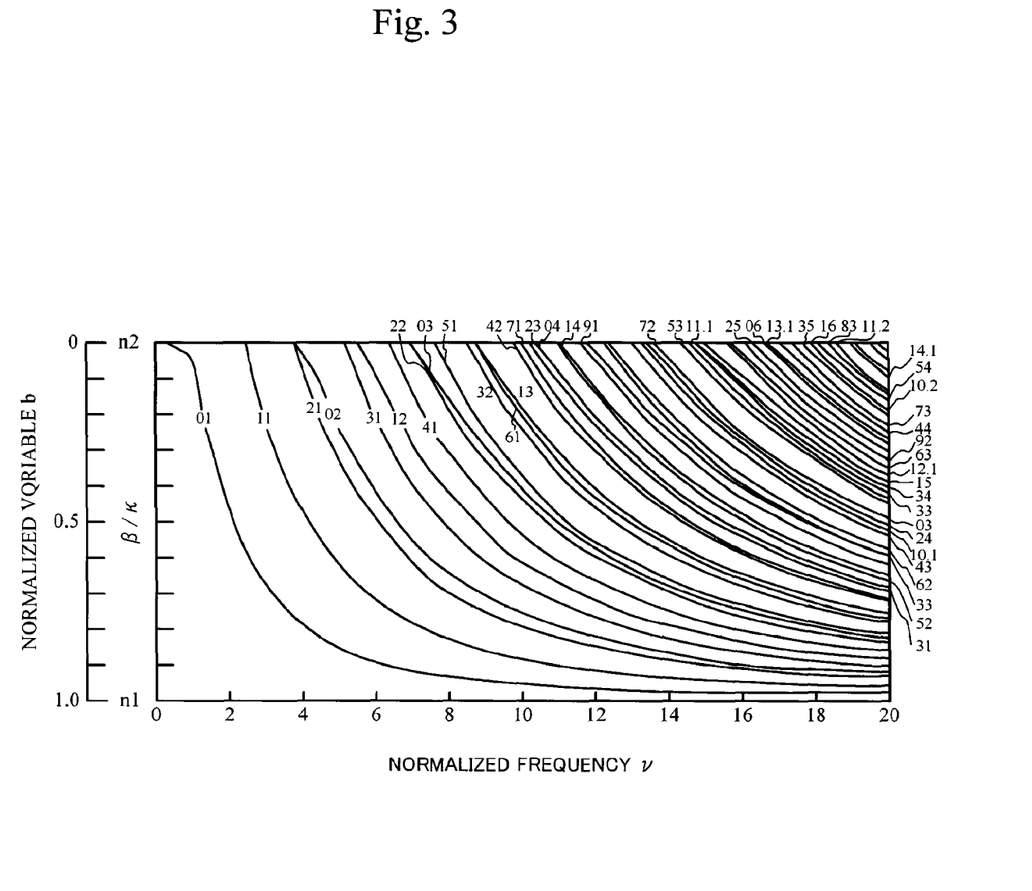
FIG. 3 shows dispersion curves of a known uniform-core optical fiber.

FIG. 3 shows dispersion curves of a known uniform-core optical fiber. The horizontal axis is the normalized frequency $\upsilon$, and the vertical axis is a normalized variable b, and shows the relation between $\upsilon$ and b in each mode. For example, the following can be seen from the dispersion curves. The 01 mode (fundamental mode) is located about b=0.8 for $\upsilon$=4, and the 11 mode (first-order mode) is located about b =0.5 for $\upsilon$=4. Further, the 21 mode is located about b=0.1 for $\upsilon$=4. The normalized frequency $\upsilon$ can be obtained by the refractive index of the oxidized region in a current funneling layer, the refractive index of the non-oxidized region in the current funneling layer, and the core diameter (the diameter of the aperture of the non-oxidized region). That is, $\upsilon = kn_1 a(2\Delta)^{1/2}$ where $\Delta$ is the difference in the refractive index between the oxidized region and the non-oxidized region, a is the radius of the core, k is a predetermined constant, and $n_1$ is the refractive index of the non-oxidized region. The normalized variable b indicates the degree of confining optical power in each mode, as illustrated in FIGS. 4A through 4C.

For example, the first-order single-mode VCSEL may be designed as follows. First, the material of the current funneling layer of VCSEL is selected. The refractive index of the oxidized region and that of the non-oxidized region are physically determined by selecting the material of the current funneling layer. As will be described later, the VCSEL 112 uses AlAs to form the current funneling layer, and the refractive indexes of the oxidized region and the non-oxidized region are physically determined. Second, the dispersion curves illustrated in FIG. 3 are referred to in order to determine the normalized frequency υ and the normalized variable to realize the first-order (11 mode) oscillation. For the normalized frequency υ, the core diameter (2a) is obtained from the refractive indexes of the oxidized region and the non-oxidized region determined at the first step. Third, the distribution of the emission powers of the existing modes can be obtained from the normalized variable b. Since the first-order single-mode VCSEL is used, the normalized variable b of the 11 mode is obtained.

Figure 4A:
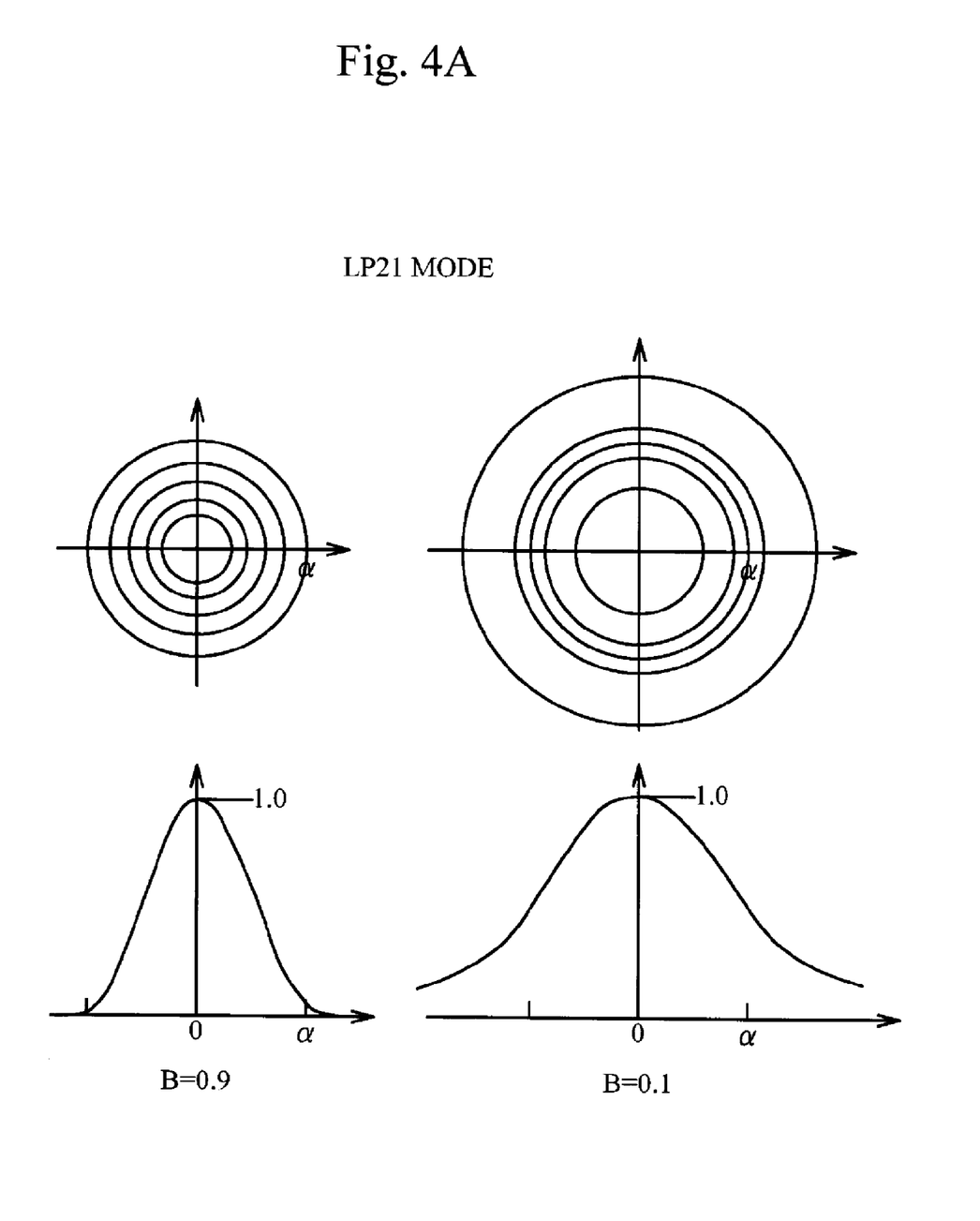
FIG. 4A illustrates power distributions of normalized light of LP01 mode for b=0.9 and b=0.1.
Figure 4B:
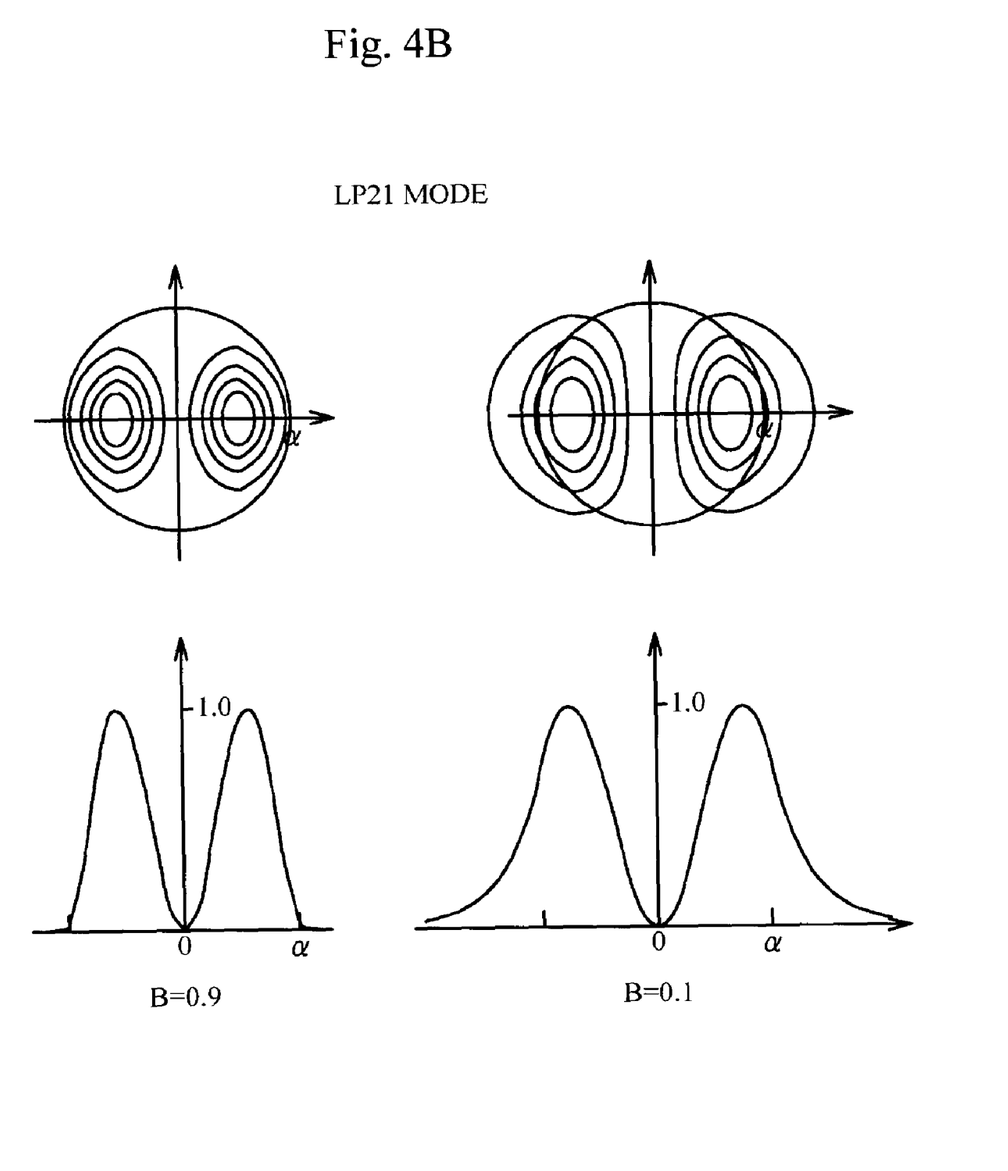
FIG. 4B illustrates power distributions of normalized light of LP11 mode for b=0.9 and b=0.1.
Figure 4C:
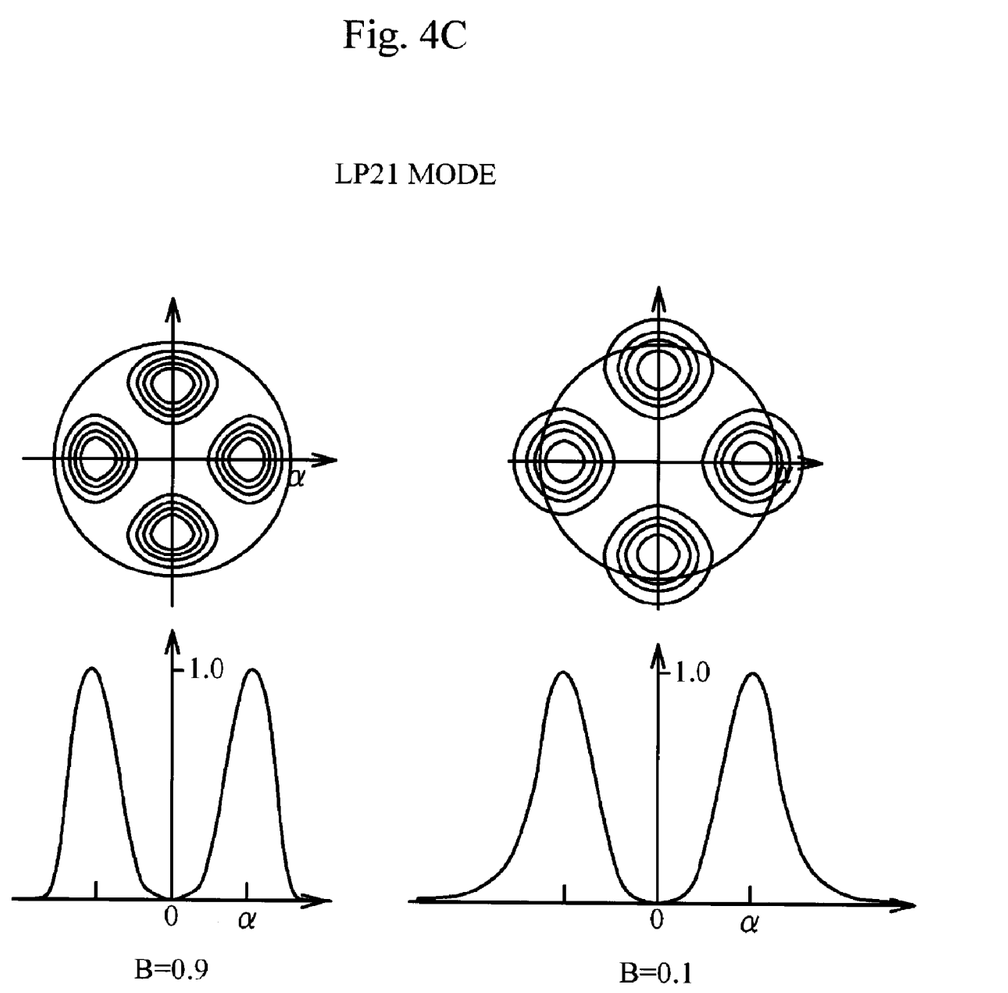
FIG. 4C illustrates power distributions of normalized light of LP21 mode for b=0.9 and b=0.1.

FIG. 4A illustrates power distributions of normalized light of LP01 mode for b=0.9 (the optical energy is confined well) and b=0.1 (close to the cutoff state). FIG. 4B illustrates power distributions of normalized light of LP11 mode for b=0.9 and b=0.1. FIG. 4C illustrates power distributions of normalized light of LP21 mode for b=0.9 and b=0.1. Referring to FIG. 4B, for b=0.9, there are observed two single-peak laser beams having a small spreading angle or radiating angle with respect to the optical axis. For b=0.1, there are observed two single-peak laser beams having a large spreading angle and a comparatively gentle slope. It is thus possible to detect the radiation angles of the peaks of the light intensity that depend on the normalized variable b or to detect the positions of the peaks of the light intensity with respect to the optical axis. Thus, the pattern of the emission electrode or the groove can be defined on the basis of the radiation angles or the positions of the peaks.

Figure 5A:
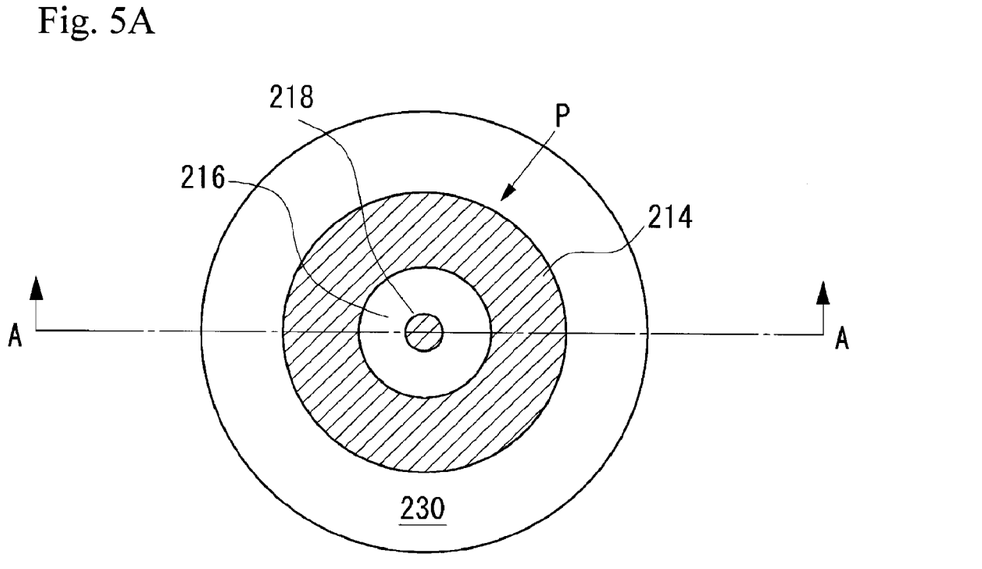
FIG. 5A is a plan view of a VCSEL illustrated in FIG. 2.
Figure 5B:
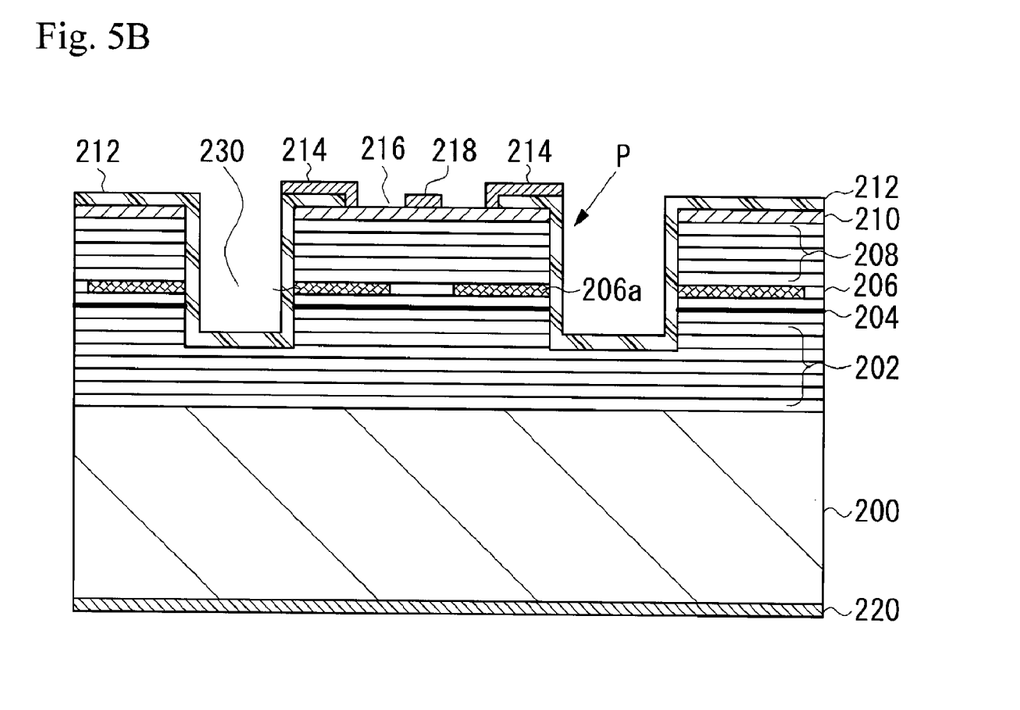
FIG. 5B is a cross-sectional view taken along a line A-A.

FIG. 5A is a plan view of the VCSEL 112, and FIG. 5B is a cross-sectional view taken along a line A-A illustrated in FIG. 5A. An electrode layer is depicted with hatching for facilitating better understanding in FIG. 5A. The VCSEL 112 has a GaAs substrate 200 on which there are stacked a lower DBR (Distributed Bragg Reflector) 202 formed by an n-type semiconductor multilayer, an active region 204, a p-type AlAs layer 206, and an upper DBR 208 formed by a p-type semiconductor multilayer in that order. The uppermost layer of the upper DBR 208 is a contact layer 210 of a p-type GaAs layer.

A ring-shaped groove 230 is formed so as to reach a part of the lower DBR 202 from the upper DBR 208, and defines a cylindrical post or mesa P on or above the GaAs substrate 200. The post P is thermally treated in a water vapor at a high temperature to thus define an oxidized region 206a in an outer circumferential portion of the p-type AlAs layer 206 in the post P. The oxidized region in the p-type AlAs layer 206 defines the light and current funneling region.

An interlayer insulator film 212 covers the bottom, side and a part of the top of the post P. A circular contact hole is formed in the interlayer insulator film 212 on the top of the post P. A p-side electrode layer 214 is in ohmic contact with the contact layer 210 in the contact hole. A circular emission window or aperture 216 for laser emission is formed at the center of the p-side electrode layer 214. The contact layer 210 is exposed by the emission window 216. A circular shield portion 218 for shielding light is formed on the optical axis of the center of the emission window 216. The shield portion 218 may be formed of a metal. Preferably, the shield portion 218 is made of the same material as that of the p-side electrode layer 214 and is formed simultaneously when the emission window 216 is formed in the p-side electrode layer 214. An n-side electrode layer 220 is formed on the backside of the GaAs substrate 200.

The n-type lower DBR 202 may be formed by, for example, alternately stacking an Al0.9Ga0.1As layer and an Al0.3Ga0.7As layer with multiple periods, and each of these layers is equal to $\lambda/4 n_r$ where $\lambda$ is the oscillation wavelength, and $n_r$ is the refractive index of the medium. The active region 204 may be composed of, for example, an undoped lower $Al_{0.5}Ga_{0.5}As$ spacer layer, an undoped quantum well active layer and an undoped $Al_{0.5}Ga_{0.5}As$ spacer layer. The p-type upper DBR 208 may be formed by, for example, alternately stacking an $Al_{0.9}Ga_{0.1}As$ layer and an $Al_{0.3}Ga_{0.7}As$ layer with multiple periods, and each of these layers is equal to ¼ of the wavelength in the medium. The lowermost layer of the upper DBR 208 includes the p-type AlAs layer 206 of a low resistance. The p-type GaAs contact layer 210 having a concentration of $1\times10^{19}$ cm$^{-3}$ is stacked on the uppermost layer of the upper DBR 208. The p-side electrode layer 214 may be made of, for example, Au, and the n-side electrode layer 220 may be formed of, for example, Au/Ge. The interlayer insulator film 212 may be formed of, for example, SiNx.

The post P has a vertical resonator composed of the lower DBR 202 and the upper DBR 208. A current is applied in the forward direction between the p-side electrode layer 214 and the n-side electrode layer 220, so that laser beams of a wavelength of about 850 nm can be emitted via the emission window 216 in the post P in the direction vertical to the GaAs substrate 200. The VCSEL 112 operates in the first-order single mode, and the two laser beams are emitted from the emission window 216. The two laser beams are emitted at the equal angles to the optical axis.

As has been described previously, the emission power distribution of the first-order single mode depends on the value of the normalized variable b, as illustrated in FIG. 4B. The greater the value of the variable b, the stronger the current funneling and the smaller the spreading angles of the laser beams. In contrast, the smaller the value of the variable b, the greater the spreading angles of the laser beams. The spreading angles of the laser beams are determined from the normalized variable b. The aperture diameter of the emission window 216 in the p-side electrode layer 214 is designed to have a size that allows the laser beams of the first-order single mode to pass through the emission window 216. Further, the shield portion 218 is arranged on the optical axis and is designed to block the zero-order laser beams without blocking the first-order laser beams. For example, in a case where the current funneling layer is made of AlAs, the first-order laser beams can be obtained by setting the core diameter of the conductive region surrounded by the oxidized region 206a to 4 micron and setting the diameter of the shield portion 218 to 2 micron. It is thus possible to emit, through the emission window 216, the two laser beams having the equal spreading angles with respect to the optical axis.

Figure 6A:
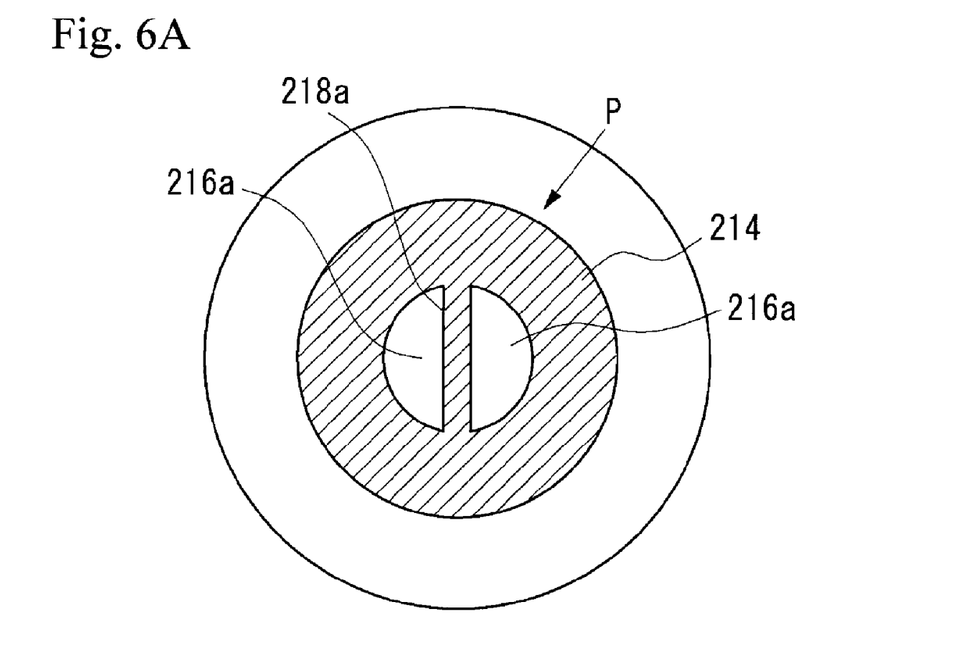
FIG. 6A is a plan view of another example of a shield part formed in an emission region of the VCSEL.

The shield portion 218 is not necessarily formed by the same material as that of the p-side electrode layer 214 but may be made of another metal capable of shielding laser. The shape of the shield portion 218 is not limited to the circle. For example, FIG. 6A illustrates a shield portion 218a, which passes through the optical axis and extends on the center of p-side the electrode layer 214 straight. The shield portion 218a defines two emission windows 216a at the right and left sides thereof.

Figure 7:
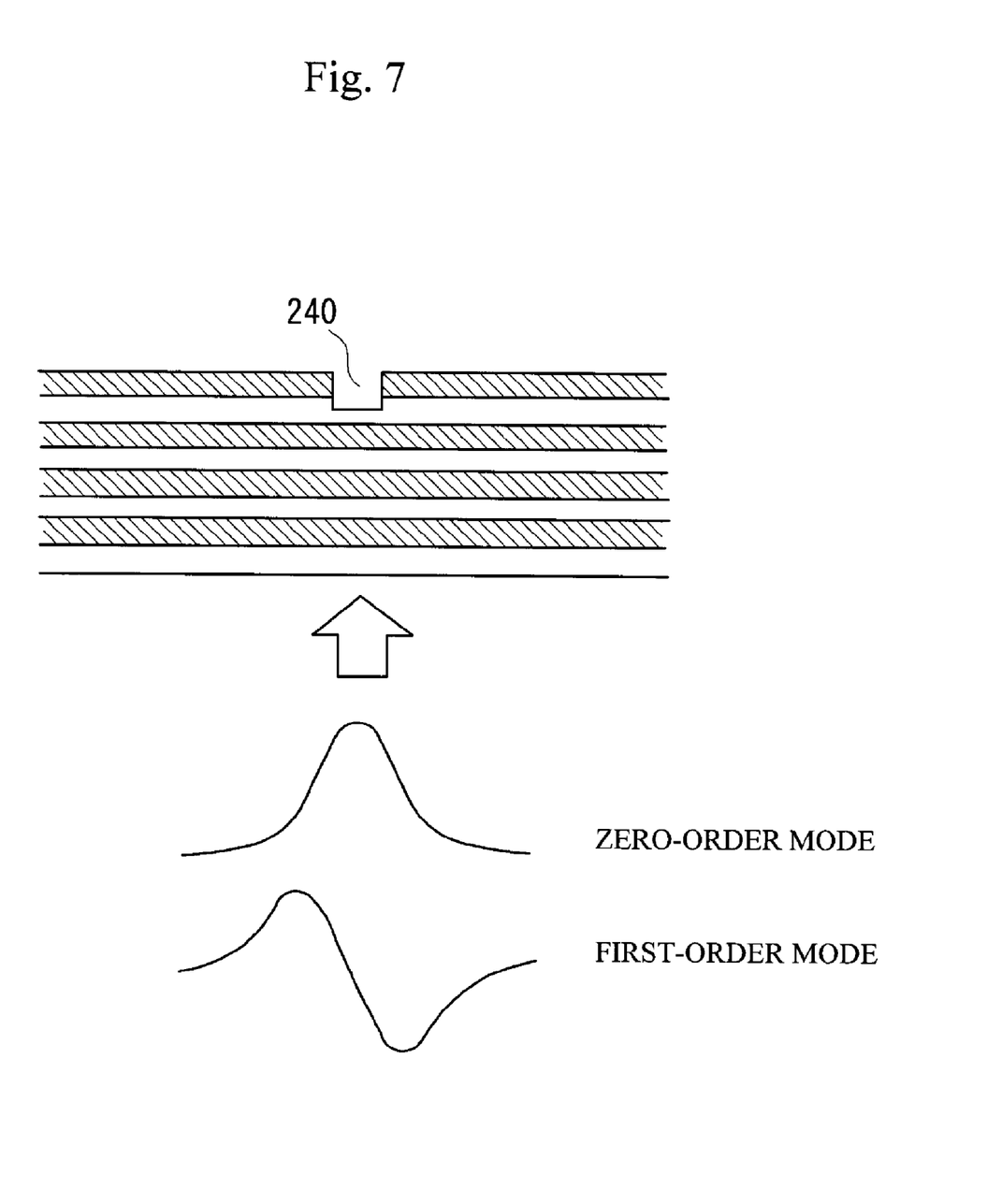
FIG. 7 illustrates a first-order single-mode laser beam produced by a trench.

The first-order single-mode VCSEL may be configured to use a groove or hole instead of the shield portion in the emission region. As illustrated in FIG. 7, a trench 240 is formed in the optical axis on the emission surface of a multilayer structure formed by stacking semiconductor layers. Thus, emission of the laser beam of the zero-order mode is suppressed by the trench 240, and laser beams of the first-order mode having an intensity distribution illustrated in FIG. 7 are emitted from the emission surface.

Figure 6B:
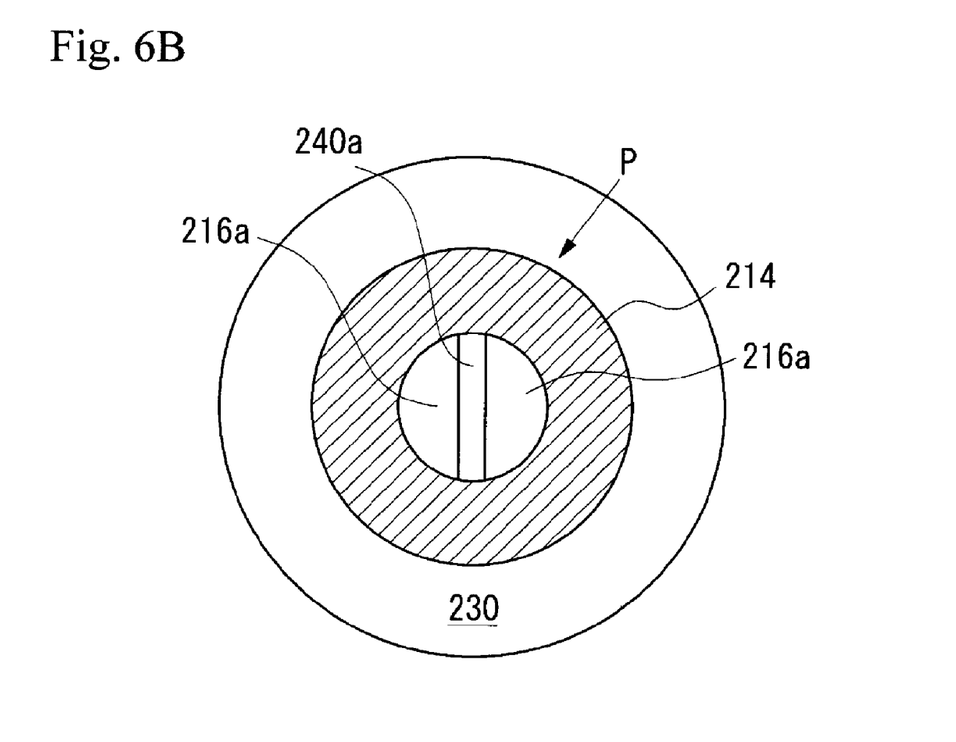
FIG. 6B is a plan view of yet another example of the shield part formed in the emission region of the VCSEL.
Figure 8A:
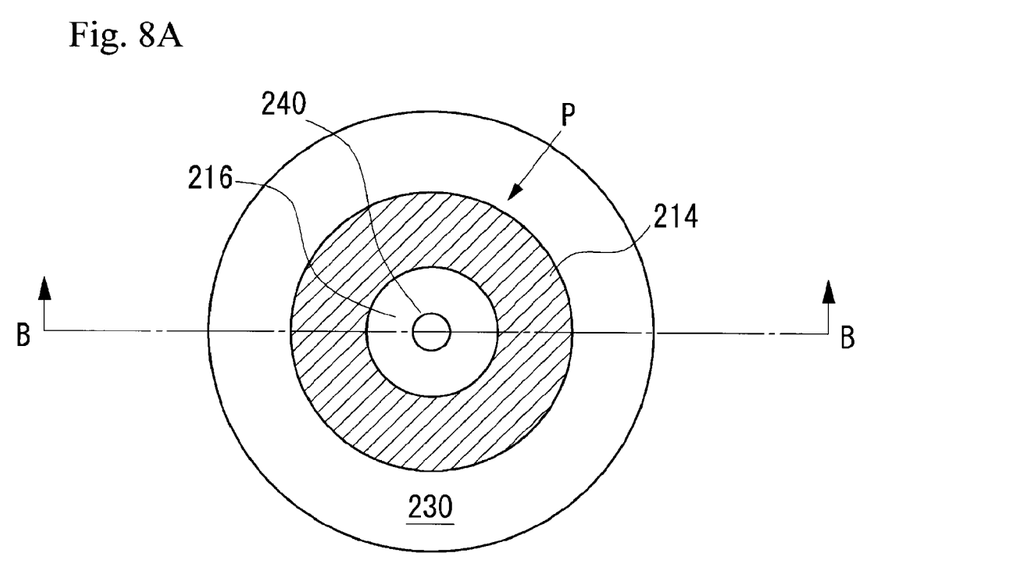
FIG. 8A is a plan view of another configuration of the VCSEL illustrated in FIG. 2.
Figure 8B:
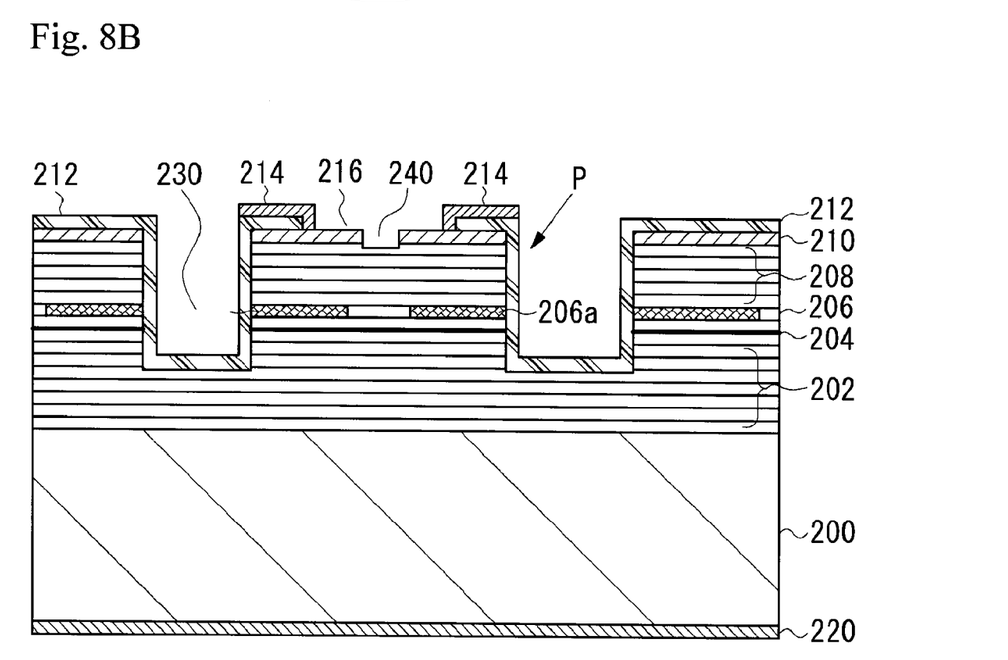
FIG. 8B is a cross-sectional view taken along a line B-B illustrated in FIG. 8A.

FIG. 8A is a plan view of a VCSEL having the trench formed on the emission surface, and FIG. 8B is a cross-sectional view taken along a line B-B in FIG. 8A. The circular trench 240 is formed on the optical axis at the center of the emission window 216. The trench 240 is designed to have a size that suppresses the laser beam of the zero-order mode and allows the laser beams of the first-order mode to pass through the trench 240. The trench 240 may be formed on the emission surface by, for example, a focused ion beam processing apparatus. The trench 240 may have a diameter of 1 micro and a depth of 1 micro. The trench 240 is not limited to the circular shape but may be shaped into a rectangle. Further, as illustrated in FIG. 6B, the trench 240a may have a shape so as to run on the optical axis and reach the electrode layer to thus divide the emission window into two emission windows 216a.

A description will now be given of the impedance change detecting circuit 120. The driving circuit 114 drives the VCSEL 112 by the driving signal of a constant frequency. The two laser beams emitted from the VCSEL 112 are projected onto the object S to be measured. The feedback lights reflected or scattered by the object S return to the laser medium of the post P, and the laser oscillation is thus modulated. A beat signal appears in the light intensity due to the difference in frequency or phase between the emitted laser beams and the feedback lights having a Doppler shift. This beat signal appears as an impedance change of the VCSEL in the driving signal. The impedance change detecting circuit 120 detects the impedance change of the VCSEL that appears in the driving signal.

By modulating the light intensity of the VCSEL by the driving circuit 114, the oscillation frequency is changed, and the beat signal is the difference between the oscillation frequency and the frequency of the feedback lights having a Doppler shift caused by the movement direction and velocity of the measured object S. The beat signal is also caused by the phase difference between the oscillation frequency and the feedback lights due to the distance to the measured object S. The frequency component analyzing circuit 130 analyzes the detected impedance change, that is, the frequency of the beat signal, and obtains the Doppler shift frequency and the phase difference regarding the two laser beams. The analyzed results by the frequency component analyzing circuit 130 are supplied to the distance/velocity calculating circuit 140, which calculates the distance, velocity and direction of the measured object S.

Figure 9:
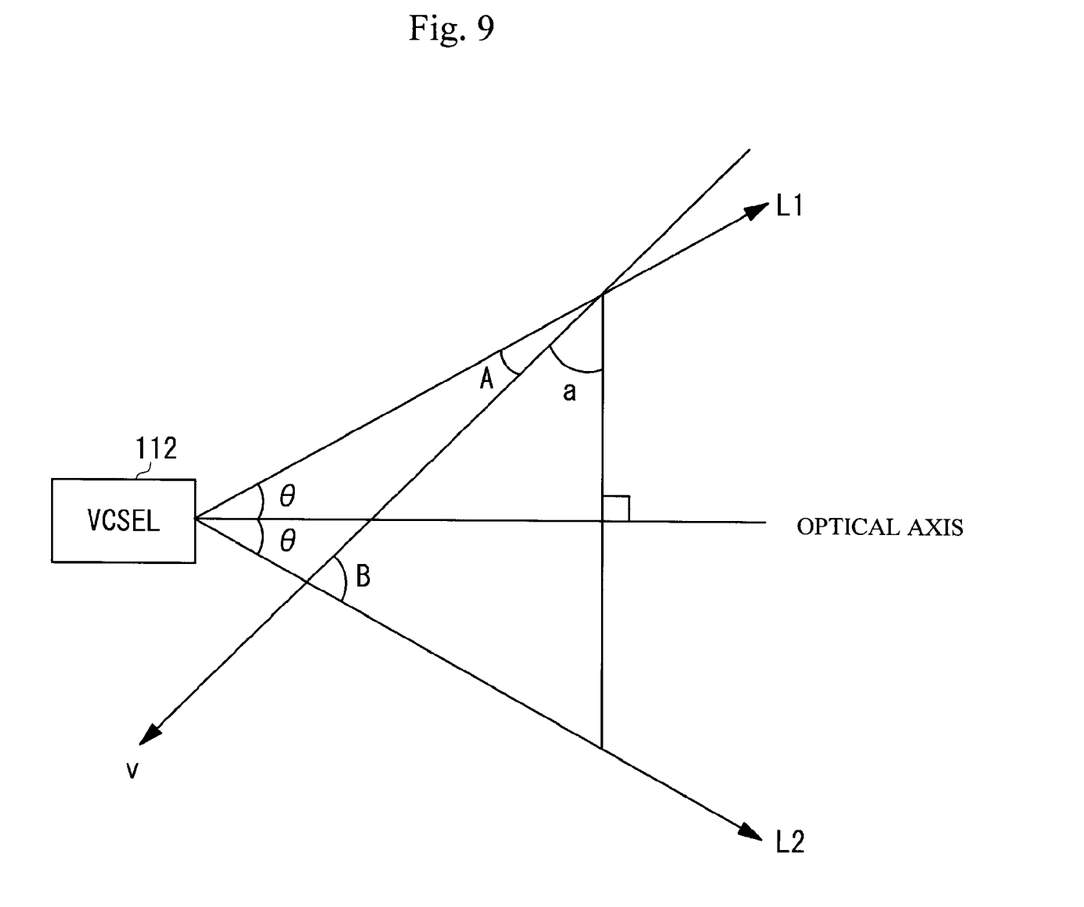
FIG. 9 illustrates a way to calculate a velocity and a moving direction of an object to be measured.

A description will now be given of an operation of the distance/velocity calculating circuit 140 in a case where the measured object S rotates at a stationary position which does not cause any change in the distance between the sensor and the measured object S and only the velocity of rotation of the object S is measured. In that case, a phase difference is not caused and only a Doppler shift is caused. FIG. 9 illustrates a way to measure the distance to the object S and the velocity thereof. The first-order single-mode VCSEL 112 emits laser beams L1 and L2 so as to be gradually away from the optical axis without using the optical waveguide and the half mirror. The radiation (emission) angles θ of the laser beams L1 and L2 with respect to the optical axis are equal to each other. The two laser beams L1 and L2 are incident to the object S at different incident angles.

When the object S is moving at a velocity v, the laser beams L1 and L2 are reflected by the moving object S, and different Doppler shifts that depend on the moving velocity v of the object S are caused in the laser beams L1 and L2. Parts of the reflected beams from the object S travel along the incident paths and return to the VCSEL 112. The feedback lights having the different Doppler shifts enter the medium of the VCSEL 112, and vary the impedance and the amount of emission of the VCSEL 112. The impedance and the amount of emission of the VCSEL 112 have two variation components (frequency components) corresponding to the respective Doppler shifts. By analyzing the two frequency components, it is possible to obtain velocity information showing the direction of movement of the object S on the two-dimensional plane including the divided laser beams and the velocity thereof. Further, the distance/velocity calculating circuit 140 is capable of differentiating the velocity to obtain the acceleration of the object S and integrating the velocity to obtain the distance of rotation of the object S.

A further description of the measurement way is described below. The known values are θ, v1 and v2 where θ is the emission angles of he laser beams L1 and L2 with respect to the optical axis, and v1 and v2 are respectively components of the velocity v of the object S in the directions of the paths of the laser beams L1 and L2. The velocities v1 and v2 may be obtained from Doppler shift frequencies f1 and f2 of the feedback lights in the paths of the laser beams L1 and L2 and an expression of $v=\lambda/2\pi f$.

The values a and v are finally obtained by the distance/velocity calculating circuit 140 where a is the moving direction (angle) of the measured object S with respect to the normal line vertical to the optical axis, and v is the velocity of the measured object S.

The velocity component v1 in the direction of the path of the laser beam L1 and the velocity component v2 in the direction of the path of the laser beam L2 are obtained from expressions (1) and (2):

$$v1 = v \cos A \tag{1}$$

$$v2 = v \cos B \tag{2}$$

where A and B are angles illustrated in FIG. 9, and are obtained from expression (3).

The angles a and A has a relation defined by expression (4):

$$B = A + 2\theta \tag{3}$$

$$a = \pi/2 - \theta - A \tag{4}$$

Expression (5) is obtained from expressions (1) and (2):

$$\cos B = (v2/v1)\cos A \tag{5}$$

Expression (6) is obtained from expression (3):

$$\cos B = \cos A \cos 2\theta - \sin A \sin 2\theta \tag{6}$$

The angle A described in expression (7) is obtained from expressions (5) and (6):

$$\tan A = \{\cos 2\theta - (v2/v1)\}/\sin 2\theta, \text{ thus}$$

$$A = \tan^{-1}[\{\cos 2\theta - (v2/v1)\}/\sin 2\theta] \tag{7}$$

The velocity v of the measured object S is obtained by expression (8) from expressions (1) and (7):

$$v = v1/\cos<\tan^{-1}[\{\cos 2\theta - (v2/v1)\}/\sin 2\theta]> \tag{8}$$

The direction of movement of the measured object S is obtained by expression (9) from expressions (4) and (7):

$$a=\pi/2-\theta-\tan^{-1}[\{\cos 2\theta-(v2/v1)\}/\sin 2\theta] \quad (9).$$

By using the above expressions, the velocity and moving direction of the object S can be obtained. According to the present embodiment, the use of the first-order single-mode VCSEL makes it easy to form the two laser beams having the emission angles primarily defined due to the structure, and avoids the fine adjustment of the positions of optical components such as the optical waveguide and half mirror. It is thus possible to obtain a less-expensive measuring device that is composed of a reduced number of parts and is manufactured by a reduced number of steps.

Although the above embodiment uses one VCSEL, multiple VCSELs may be monolithically arranged in rows and columns to measure multiple positions of the object to be measured. This arrangement improves the reliability of measurement.

The measuring device may be applied to a bloodstream measurement device capable of the velocity and quantity of hemoglobin in blood. The laser beam having a wavelength of 850 nm passes through the skin of human being and is projected onto hemoglobin in blood. Some of lights reflected or scattered on the surface of hemoglobin contribute the self-coupling effect as feedback lights, so that the velocity and direction of hemoglobin can be measured.

The measuring device of the present embodiment may be utilized as a velocity sensor or angular sensor other than the bloodstream measurement device. The present invention includes VCSELs having a wavelength other than 850 nm or having a structure other than the above described structure.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A measuring device comprising:
   a Vertical-Cavity Surface-Emitting Laser (VCSEL) of a first-order or high-order single mode emitting laser beams;
   a driving part configured to drive the VCSEL;
   a detecting part configured to detect an electric signal relating to feedback lights generated when laser beams are projected onto an object; and
   a calculating part configured to identify a direction of movement of the object on the basis of the electric signal detected by the detecting part.

2. The measuring device according to claim 1, wherein the detecting part detects the electric signal corresponding to an impedance change of the VCSEL.

3. The measuring device according to claim 1, wherein the detecting part includes an analyzing part configured to analyze, from the electric signal, frequency components representing variations of light intensities of first and second laser beams, and the calculating part calculates a velocity of the object on the basis of the frequency components analyzed.

4. The measuring device according to claim 1, wherein:
   the calculating part obtains, from expressions (1) and (2), a velocity component v1 in a direction of a path of a laser beam L1 and a velocity component v2 in a direction of a path of a laser beam L2 where θ is emission angles of the laser beams L1 and L2, v is a moving velocity v of the object, a is a moving angle of the object, and A and B are angles of the laser beams L1 and L2 with respect to a moving direction of the object;
   a relation between A and B is obtained from expression (3);
   a relation between the angles a and A is obtained from expression (4);
   expression (5) is obtained from expressions (1) and (2);
   expression (6) is obtained from expression (3);
   expression (7) is obtained from expressions (5) and (6);
   expression (8) is obtained from expressions (1) and (7); and
   expression (9) is obtained from expressions (4) and (7), $$v1=v\cos A \quad (1)$$

$$v2=v\cos B \quad (2)$$

$$B=A+2\theta \quad (3)$$

$$a=\pi/2-\theta-A \quad (4)$$

$$\cos B=(v2/v1)\cos A \quad (5)$$

$$\cos B=\cos A \cos 2\theta-\sin A \sin 2\theta \quad (6)$$

$$\tan A=\{\cos 2\theta-(v2/v1)\}/\sin 2\theta, \text{ thus}$$

$$A=\tan^{-1}[\{\cos 2\theta-(v2/v1)\}/\sin 2\theta] \quad (7)$$

$$v=v1/\cos<\tan^{-1}[\{\cos 2\theta-(v2/v1)\}/\sin 2\theta]> \quad (8)$$

$$a=\pi/2-\theta-\tan^{-1}[\{\cos 2\theta-(v2/v1)\}/\sin 2\theta] \quad (9).$$

5. The measuring device according to claim 1, wherein:
   the VCSEL includes a substrate, a first reflector of a semiconductor multilayer of a first conduction type, an active region, a second reflector of a semiconductor multilayer of a second conduction type, and an electrode layer provided on the second reflector;
   the electrode layer has an emission window through which first and second laser beams of a first-order mode are emitted; and
   the VCSEL includes a shield portion that is provided in the emission window and shields a laser beam of a zero-order mode.

6. The measuring device according to claim 1, wherein:
   the VCSEL includes a substrate, a first reflector of a semiconductor multilayer of a first conduction type, an active region, a second reflector of a semiconductor multilayer of a second conduction type, and an electrode layer provided on the second reflector;
   the electrode layer has an emission window through which first and second laser beams of a first-order mode are emitted; and
   a groove for suppressing a laser beam of a zero-order mode is formed in the second reflector exposed in the emission window.

7. The measuring device according to claim 1, wherein:
   the VCSEL emits first and second laser beams of a wavelength of 850 nm, and are projected onto hemoglobin in blood; and
   the calculating part calculates a velocity of hemoglobin in blood.

8. The measuring device according to claim 7, further comprising a display part on which the velocity of hemoglobin in blood is displayed.

* * * * *